(12) United States Patent
Deininger (10) Patent No.: US 11,231,402 B2
(45) Date of Patent: Jan. 25, 2022

(54) CALIBRATED MOBILE GAS SENSOR (71) Applicant: Integrated Device Technology, Inc., San Jose, CA (US)

(72) Inventor: Debra J. Deininger, San Jose, CA (US)

(73) Assignee: Integrated Device Technology, Inc., San Jose, CA (US)

( * ) Notice: Subject to any disclaimer, the term of this patent is extended or adjusted under 35 U.S.C. 154(b) by 619 days.

(21) Appl. No.: 16/020,836

(22) Filed: Jun. 27, 2018

(65) Prior Publication Data

US 2018/0372703 A1 Dec. 27, 2018

Related U.S. Application Data (60) Provisional application No. 62/525,622, filed on Jun. 27, 2017.

(51) Int. Cl.
*G01N 33/00* (2006.01)

(52) U.S. Cl.
CPC ....... *G01N 33/0008* (2013.01); *G01N 33/007* (2013.01); *G01N 2033/0072* (2013.01)

(58) Field of Classification Search
CPC .......................... G01N 33/0008; G01N 33/007
USPC .......................................................... 702/104
See application file for complete search history.

(56) References Cited

U.S. PATENT DOCUMENTS

| 9,612,195 | B1* | 4/2017 | Friedman | ............. | G01N 33/004 |
| 9,721,456 | B2* | 8/2017 | Thurlow | ............... | H04W 4/029 |
| 2014/0238100 | A1* | 8/2014 | Londergan | ......... | G01N 33/0006 |
| | | | | | 73/1.03 |

* cited by examiner

*Primary Examiner* — Aditya S Bhat
(74) *Attorney, Agent, or Firm* — Haynes and Boone, LLP (57) ABSTRACT A mobile gas monitor is presented. In accordance with some embodiments, a mobile gas monitor includes a gas sensor; a mobile device coupled to the gas sensor, the mobile device executing instructions to: read data from the gas sensor; provide calibration; and provide calibrated concentrations based on the data from the gas sensor.

15 Claims, 7 Drawing Sheets

CALIBRATED MOBILE GAS SENSOR

RELATED APPLICATIONS

This application claims priority to U.S. Provisional Application 62/525,622, filed on Jun. 27, 2017, which is herein incorporated by reference in its entirety.

TECHNICAL FIELD

Embodiments of the present invention are related to mobile sensors and, in particular, to calibration of mobile gas sensors.

DISCUSSION OF RELATED ART

There is significant interest in adding gas sensor functionality to mobile phones or wearable devices. Some applications, for example detection of volatile organic compounds (VOC), bad or unpleasant air, bad orders, and certain kinds of breath measurements, require only relative measurements. However, some applications require an accurate measurement, for example a quantified measurement relative to an external standard. Examples of applications where an accurate numeric measurement is of use include, for example, detection of carcinogens (e.g., formaldehyde, benzene, or other gasses), detection of safety gases (e.g., carbon monoxide, methane or natural gas leak detection), or detection of health gases (e.g., acetone for weight loss and diabetes).

However, it is generally widely accepted that in order to deploy a sensor in a mobile phone or a wearable device, it cannot be calibrated. This appears to be a strongly held belief and limits the applications of gas sensors in cell phones. This limitation limits the potential market because the features that can be offered in a low cost, relative sensor are very limited.

Therefore, there is a need to develop sensors and sensor systems for mobile phones or wearable devices that are appropriate for accurate numeric measurements of various gases.

SUMMARY

In accordance with some embodiments of the present invention, a mobile gas monitor is presented. In accordance with some embodiments, a mobile gas monitor includes a gas sensor; a mobile device coupled to the gas sensor, the mobile device executing instructions to: read data from the gas sensor; provide calibration; and provide calibrated concentrations based on the data from the gas sensor.

A method of operating a mobile gas sensor according to some embodiments includes initializing a calibration; receiving data from a sensor of the mobile gas sensor; and providing calibration parameters based on the data from the sensor.

These and other embodiments are further discussed below with respect to the following figures.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various changes may be made without departing from the spirit and scope of this description and the claims. In some instances, well-known structures and techniques have not been shown or described in detail in order not to obscure the invention.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

As discussed above, some applications for gas sensors, such as detection of VOC & "bad/unpleasant air", bad odors, certain kinds of breath measurements, can use gas sensor capable of a relative measurement of concentrations. Other applications for gas sensors use an accurate measurement, which can be a quantified measurement relative to an external standard. Such applications, for example detection of carcinogens (e.g. formaldehyde, benzene), Detection of safety gases (e.g. carbon monoxide, methane/natural gas leak detection), Detection of health gases (e.g. acetone for weight loss & diabetes), and other types of measurements need to be accurate in order to be useful.

It is very widely accepted that in order to deploy a sensor in a mobile phone or wearable device, it cannot be calibrated. This appears to be a strongly held belief and limits the applications of gas sensors in cell phones, thus, limiting the potential market because the features that can be offered in a low cost/relative sensor are very limited. If the sensor inside a mobile phone or wearable device could be made accurate, then the value of the sensor inside a phone or wearable would be enhanced. The manufacturers would be able to offer two levels of sensor performance: a relative measurement for the "Average" user with no specific interest, and a calibration routine/kit for the subset of the customer population who desires a more specific measurement.

Embodiments of the present invention provide for a sensor in a mobile device, wearable device, or other consumer device that can be calibrated in order to provide accurate gas concentration measurements. Further, embodiments of the present invention include a method of calibration that can be used to calibrate sensors incorporated into a mobile, wearable or other consumer device, enabling accurate measurement of chemicals in breath and in air. Further, embodiments of the present invention include a method of using that calibration information to change the function of a sensor from a relative "indicator" device, to an accurate concentration sensor.

Figure 1A:
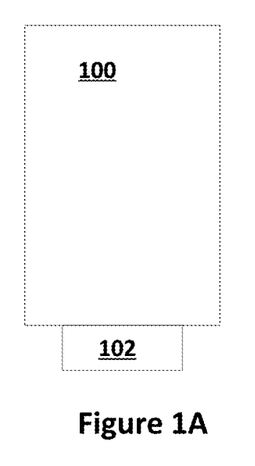
FIGS. 1A and 1B illustrate an example mobile device with a gas sensor.
Figure 1B:
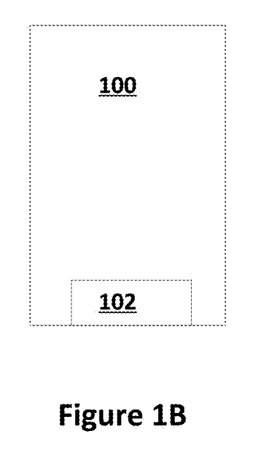

FIGS. 1A and 1B illustrate a mobile sensor device according to some embodiments of the present invention. In FIG. 1A, sensor 102 is an attachable device coupled to a mobile device 100, which may for example be a smartphone, table, laptop, or other device. For example, sensor 1A can be physically attached to mobile device 100 through, for example, a universal serial bus (USB) port or may be wirelessly coupled to mobile device 100, for example using Bluetooth. As such, in the example illustrated in FIG. 1A, sensor 102 is a removable attachment to mobile device 100.

FIG. 1B illustrates an example where sensor 102 is embedded within mobile device 100. As such, in the example illustrated in FIG. 1B, sensor 102 is not removable from mobile device 100 and is always present.

Figure 1C:
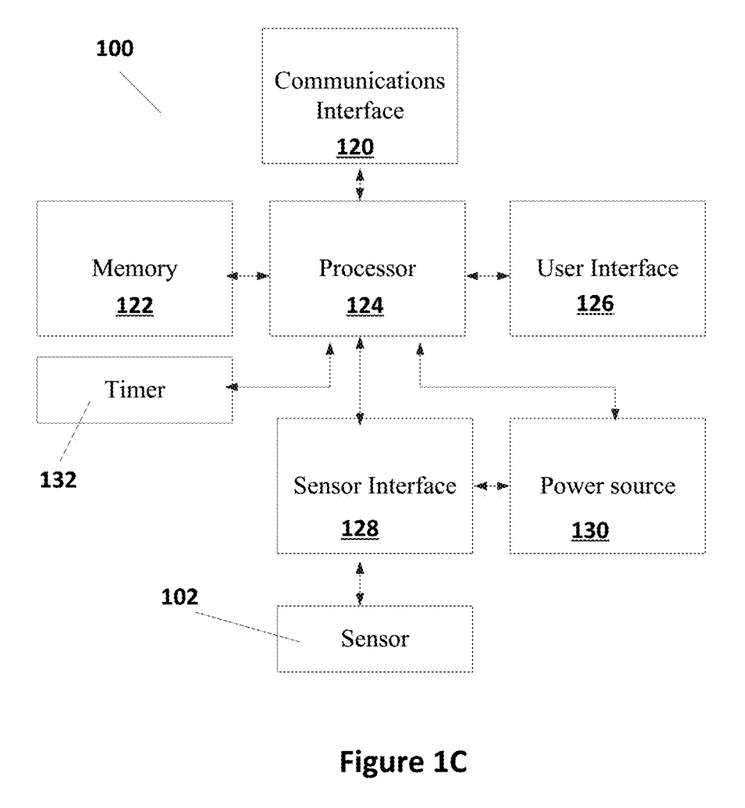
FIG. 1C illustrates interaction between the mobile device and the gas sensor depicted in FIGS. 1A and 1B.

FIG. 1C further illustrates mobile device 100 in interaction with sensor 102. As discussed above, mobile device 100 can be a smart phone, laptop computer, tablet, PDA, wearable device, or a mobile device dedicated to sensor technology. As illustrated in FIG. 1C, mobile device 100 includes a processor 124 coupled with a memory 122. Processor 124 can be any microcomputer, microprocessor, or processing device that is capable of performing the functions described below. Memory 122 can be a combination of volatile and non-volatile memory capable of storing programming executed by processor 124 and data. In some cases, memory 122 can include removable storage such as a hard drive, removable memory drive, or other device.

Processor 124 is also coupled to a user interface 126. User interface 126 can include any combination of display devices and data input devices. Display devices, for example, can include bar indicators, display screens, individual lights such as LEDs, audio devices, and the such. User input devices can include keyboards, touch screens, individual switching devices, or other input devices.

In some embodiments, processor 124 is coupled to a communications interface 120. Communications interface 120 can be, for example, wireless cell phone communications, wireless internet communications, Bluetooth or other types of wireless communications, or can represent wired communications such as USB or other interfaces.

The combination of processor 124, memory 122, user interface 126, and communications interface 120 represents an architecture commonly found in portable devices such as cell phones and other devices. As is further illustrated in FIG. 1C, processor 124 is also coupled to a sensor interface 128, which couples processor 124 with sensor 102, and power source 130. In embodiments where sensor 102 is a removable attachment, such as is illustrated in FIG. 1A, sensor interface 128 can, for example, be a USB connection. Power source 130 can be the standard power supply that supplies power to sensor 102 through sensor interface 128. In embodiments such as that illustrated in FIG. 1B, where sensor 102 is embedded in mobile device 100, sensor interface 128 is an internal circuit coupled to processor 124 that provides an interface to sensor 102. In such systems, power source 130 can provide switchable power to sensor interface 128 to power sensor 102. Processor 124 can also be coupled to a timer 132, where a time period can be set.

Figure 1D:
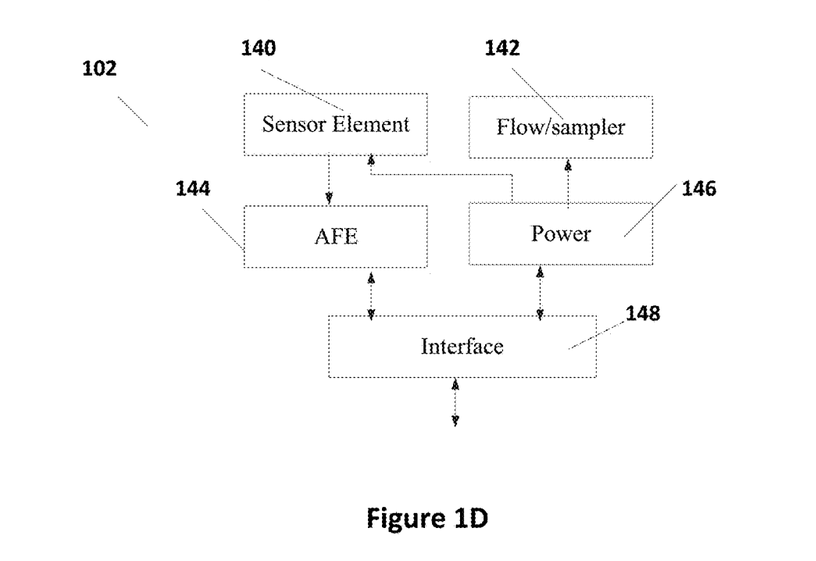
FIG. 1D illustrates an example of the gas sensor illustrated in FIGS. 1A, 1B, and 1C.

FIG. 1D illustrates an example of a sensor 102. As illustrated in FIG. 1D, sensor 102 has a gas sensor element 140. Gas sensor element 140 can be any sensor for measuring gas concentrations. Some of the common types of sensors that can be used including electrochemical (which include a porous member that allow diffusion of gas that is then chemically oxidized or reduced on an electrode causing a current change in the electrode), catalytic bead or pellistor detectors (which includes active and reference beads with platinum wire coils situated on opposite arms of a Wheatstone bridge circuit and electrically heated to a few hundred degrees), photoionization (which requires a high energy UV lamp and is not suitable for some mobile applications), infrared point or infrared imaging (that uses infrared technology to detect gas concentrations), semiconductor detectors, e.g. MOSFET detectors (which detect interactions between the gas and the semiconductor chip of the detector), ultrasonic detectors (that detects the acoustic emission of gas expansions through a small orifice), and holographic (light reflection from a hologram that diffuses the light and allows for a spectral analysis of the gas). Other detector types may also be used, but in general each involves powering sensor element 140, exposing power sensor element 140 to a volume of gas, and measuring the response of sensor element 140 to the volume of gas.

As is illustrated in FIG. 1D, sensor element 140 is coupled to a power source 146, which supplies all the power requirements that make the particular type of sensor element 140 operate. In some embodiments, a flow/sampler 142 can also be powered by power source 146 in order to either flow gas across sensor element 140 or sample and hold gas in contact with sensor element 140, as is needed to operate sensor 102.

Sensor element 140 is also coupled to an analog-front-end (AFE) 140, which receives the data signals from sensor element 140, applies analog filtering, amplification, and other processing, and digitizes the data signal. Interface 148 is coupled to both power 146 and AFE 144 in order to provide power and data interface with mobile device 100 as is illustrated in FIG. 1C. Interface 148 can be coupled to or a part of sensor interface 128.

Figure 2:
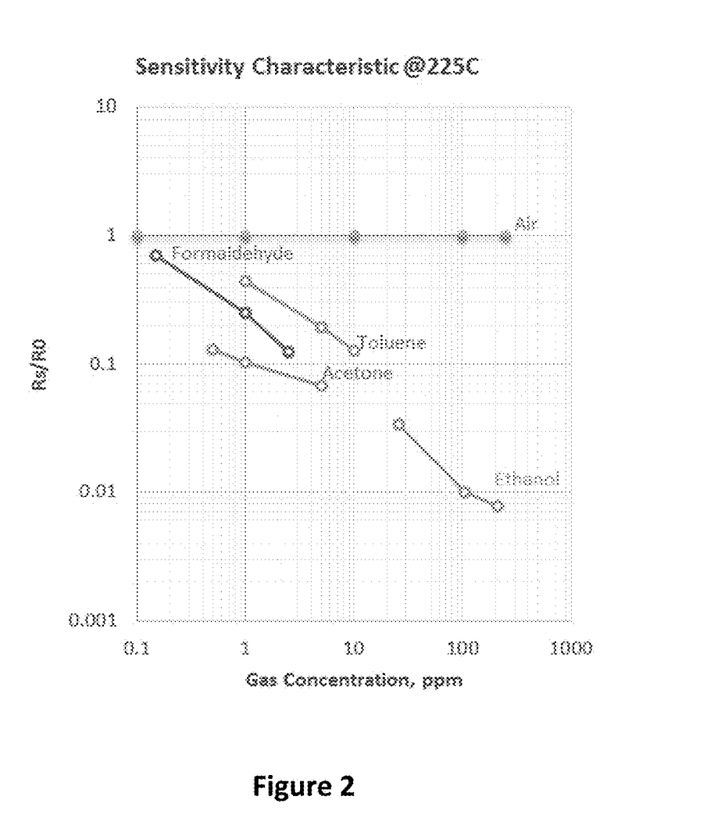
FIG. 2 illustrates an example of sensor sensitivity to various gas concentrations.

As discussed above, in order for sensor 102 to operate in an absolute fashion to provide actual concentrations of gasses detected, as opposed to measuring the presence of such gasses, a calibration process is needed. FIG. 2 illustrates an example calibrated response of a gas sensor with respect to gas concentration for air, formaldehyde, toluene, acetone and ethanol. The graph illustrates an example sensor response with respect to gas concentration for the gas shown. Consequently, to make an accurate mobile gas detector with sensor 102 and mobile device 100, a calibration method is provided according to some embodiments.

Figure 3:
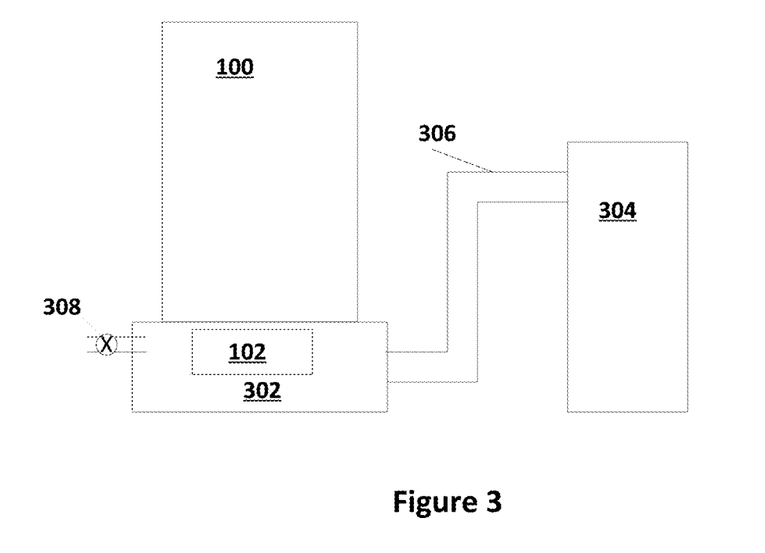
FIG. 3 illustrates an apparatus for calibrating a mobile device with a gas sensor.

FIG. 3 illustrates a calibration device that can be used for calibrating a sensor 102 that is either embedded in or attached to mobile device 100. As illustrated in FIG. 3, a chamber 302 is positioned to enclose sensor 102, which as discussed with respect to FIGS. 1A and 1B above is coupled or incorporated within mobile device 100. A source 304 is coupled to chamber 302 by a hose 306. Further, chamber 302 may be vented with a valve 308. Source 304 may be, for example, a container of test gas or vaporizable liquid. In some cases, for example calibrating for formaldehyde, source 304 is a surrogate, i.e. another volatile gas or mixture which elicits a response in sensor 102 that is similarly to the target gas, but which is safe for consumer handling.

Chamber 302 can be used to introduce the source gas to sensor 102 on mobile device 100 in a controlled fashion. As such, chamber 302 completely encloses sensor 102 and seals so that it can be flooded with gas from source 304 through hose 306 in a controlled way and at one or more controlled concentrations. Valve 308 can be used to insure that the concentration of gas from source 304 in chamber 302 can be set to a calibration concentration. Mobile device 100 can be set to a calibration mode and calibrated according to the calibration concentration of gas from known source 304.

Figure 4:
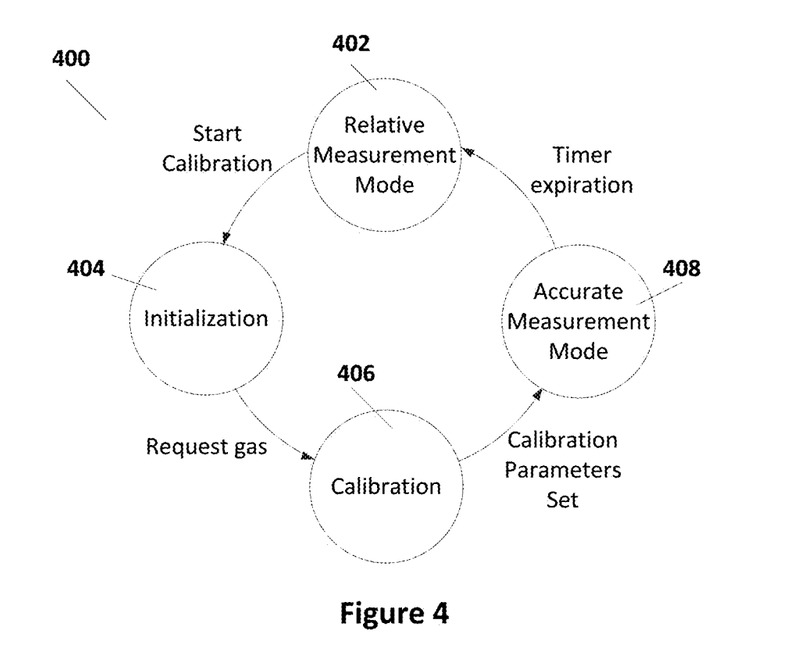
FIG. 4 illustrates a state function of mobile device with a gas sensor that can be calibrated of FIG. 3.

FIG. 4 illustrates a state diagram 400 for an application operating on mobile device 100. When mobile device 100 is coupled to receive data from sensor 102, mobile device 100 may execute instructions according to state diagram 400. Mobile device 100 may, most often, be in a relative measurement mode 402 portion of state diagram 400. In relative measurement mode 402, mobile device 100 provides a non-calibrated indication of whether or not a target gas is present and an indication of concentration. This indication is not accurate, but is sufficient for many uses.

Figure 5A:
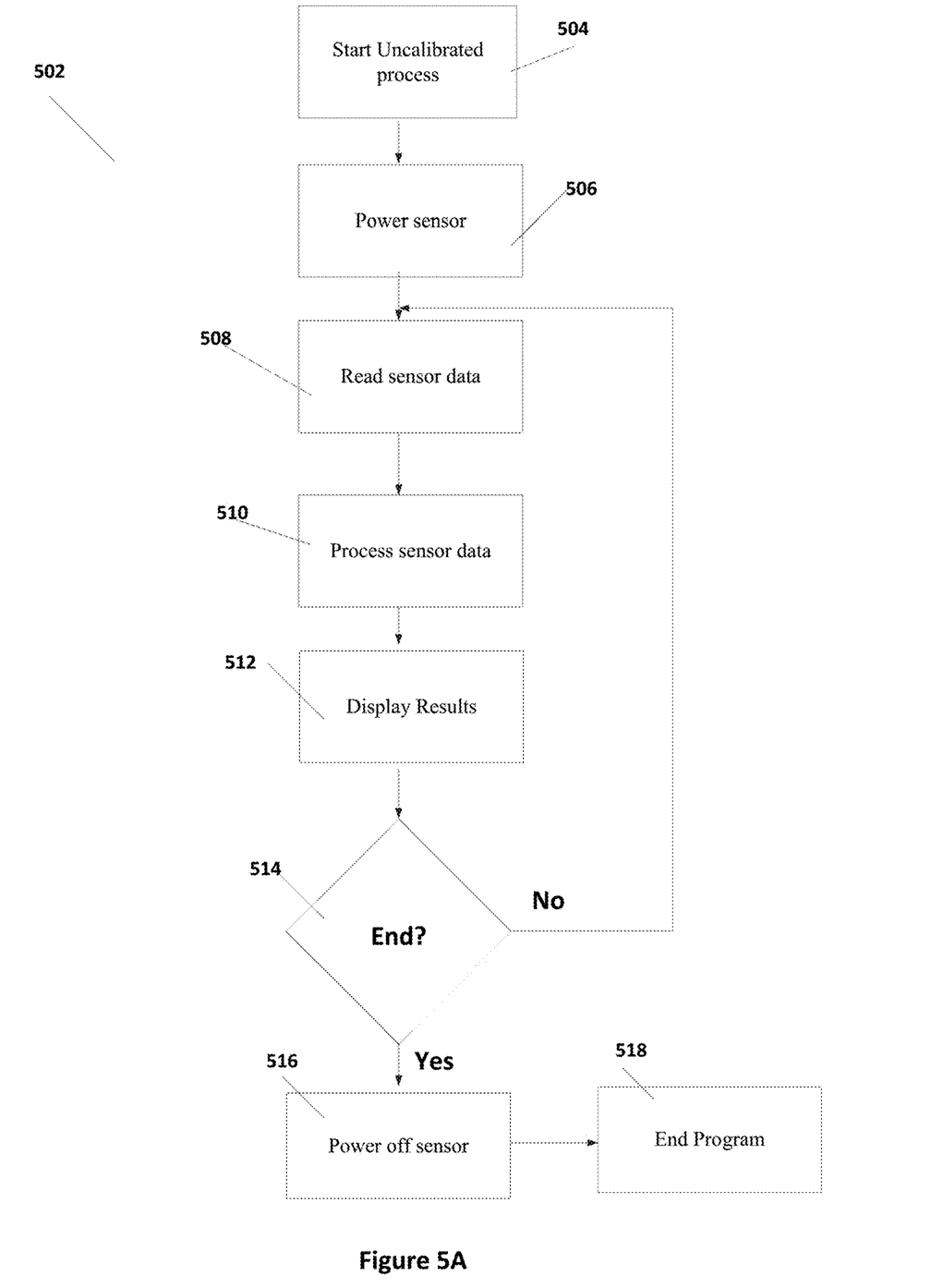
FIGS. 5A through 5D illustrate example algorithms that can be executed in each of the states of the state diagram illustrated in FIG. 4.

An example of an algorithm that can be executed by processor unit 124 of mobile device 100 in the relative measurement mode 402 of state diagram 400 is presented in FIG. 5A. Algorithm 502 starts at step 504 when a request for a gas measurement is made through user interface 126. Algorithm 502 then proceeds to step 506 where appropriate power is applied to sensor 104 as discussed above. In step 508, sensor data is read by processor 124 through interface 128. In step 510, the sensor data is processed, for example to convert the raw sensor data into concentration data. In step 512, the sensor data can be displayed, for example on user interface 126, to provide the user data on the concentration. In some embodiments, the sensor data may also be stored.

In step 514, algorithm 502 determines whether the test is completed or not. In some cases, only a single sensor data may be taken each time algorithm 502 is implemented. In some cases, algorithm 502 may repeatedly take data until the user exits algorithm 502. In step 514, if algorithm 502 is not ended, algorithm 502 returns to step 508. Otherwise, algorithm 502 proceeds to step 516.

In step 516, algorithm 502 powers off sensor 102. Algorithm 502 then proceeds to step 518, where algorithm 502 is ended.

As discussed above, if a more accurate measurement is desired, a calibration procedure can be initiated on mobile device 100. Upon a request for calibration, state diagram 400 transitions to an initiation mode 404. During initiation mode 404, mobile device 100 executes instructions to start the calibration procedure, including entering the type of gas from calibration source 304 and its concentration, requesting the user to mount chamber 302 over source 102, and performing other tasks associated with setting up the calibration. When initiation mode 404 requests that gas from source 304 is entered, state diagram 400 transitions to calibration mode 406.

Figure 5B:
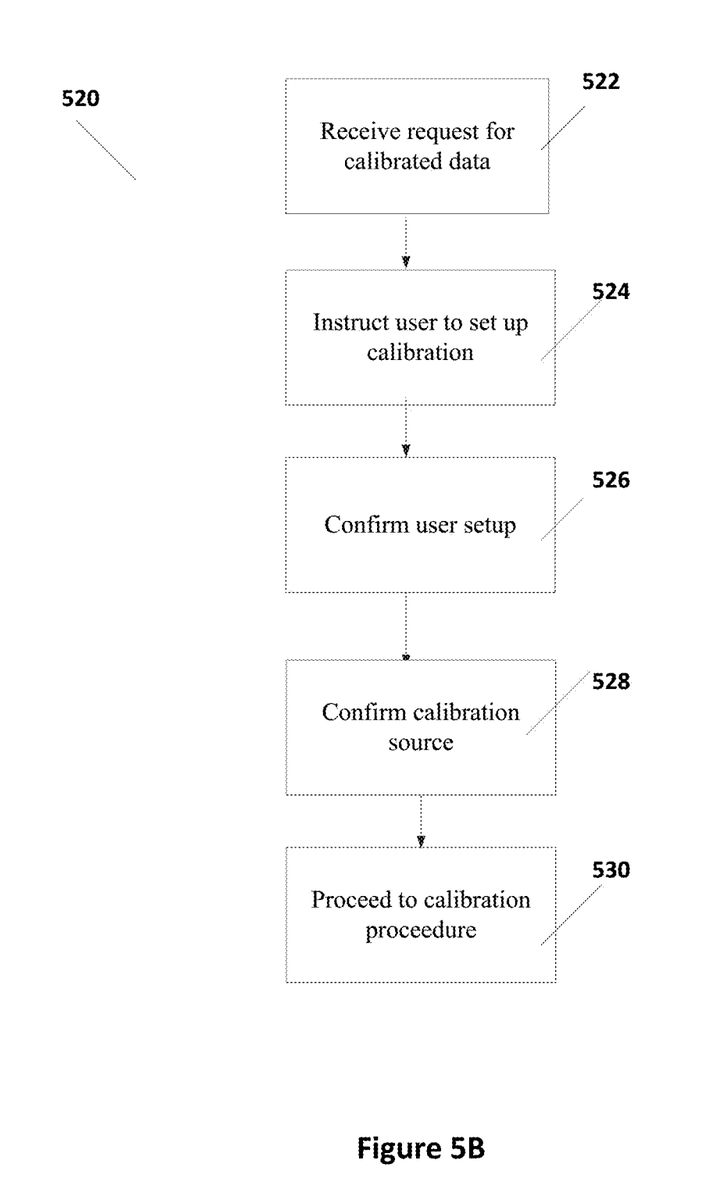

An algorithm 520 for execution of initiation mode 404 is illustrated in FIG. 5B. In step 522, a request for calibrated operation is received. In step 524, algorithm 520 provides instructions on user interface 126 for user to set up the calibration system as is illustrated in FIG. 3. As described in FIG. 3, these instructions include directions for connecting chamber 302 and attaching source 304 to chamber 302. In step 526, algorithm 502 receives a confirmation from the user through user interface 126 that the calibration system is assembled. In step 528, algorithm 520 confirms with the user the identity of the calibration source 304. At this point, algorithm 522 can store data related to the concentration of the test gas received from calibration source 304. In step 530, algorithm 520 with calibration setup and state function 400 can transition to calibration state 406.

In calibration mode 406, after chamber 302 is filled with gas at a particular known concentration from source 104, one or more measurements of the gas is taken from sensor 102. As shown in FIG. 2, each gas has a particular response characteristic as a function of gas concentration. In the example illustrated in FIG. 2, the response is a resistance change. The characteristics of the response of sensor 102 with respect to concentration is known. The calibration is then set by mobile device 100 so that mobile device 100 indicates the correct concentration value for the concentration and type of gas in source 104. In some embodiments, calibration can be accomplished at more than one concentration level in order to better calibrate the response of sensor 102.

Once calibration is complete in mode 406, mobile device 100 can then operate sensor 102 in a calibrated fashion to provide accurate measurement values. State function 400 can calibrate by scaling the data received from sensor 102 or by adjusting the processing parameters used to process the sensor data received by sensor 102. Calibration parameters can be recorded in memory 122 and used in the application operating on mobile device 100.

Figure 5C:
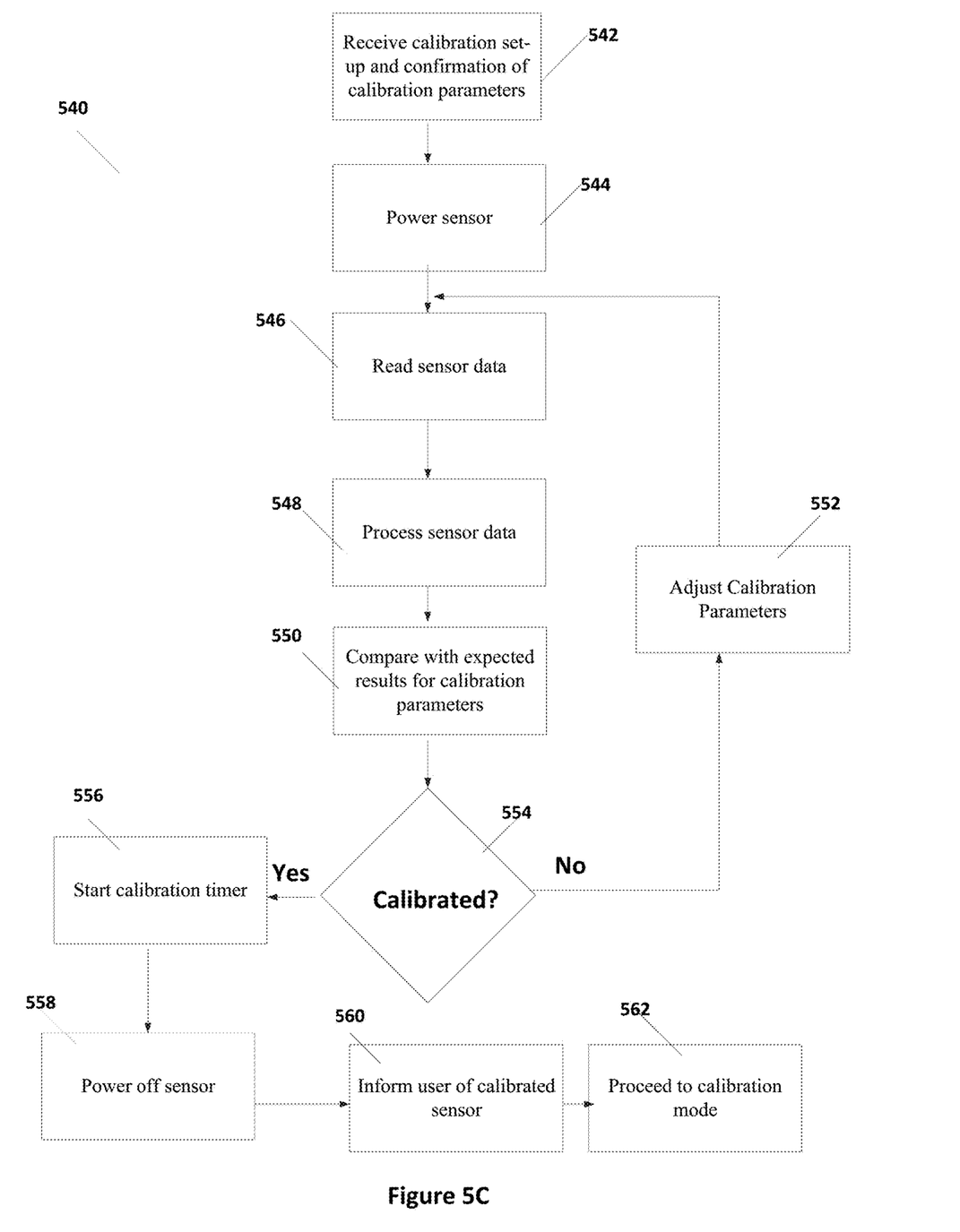

FIG. 5C illustrates an algorithm 540 for calibrating sensor 102. Algorithm 540 executes after the initialization algorithm 520 illustrated in FIG. 5B is executed. Algorithm 540 starts in step 542 where the parameters associated with the particular calibration setup are received. These parameters can include the known response characteristics of sensor 102 to the gas provided for calibration in source 304 and the known concentration of the gas provided by source 304. In step 544, sensor 102 is powered. In step 546, sensor data is received from sensor 102.

In step 548, the sensor data is processed according to the currently stored parameters to arrive at a test result. In step 550, the test result is compared with the calibrated expected results. In step 554, algorithm 540 compares the test result with the calibrated expected results. If they do not match, then algorithm 540 can proceed to step 552 to adjust calibration parameters and then return to step 546 to check the results again. In some embodiments, algorithm 540 can simply adjust the parameters and proceed to step 556, avoiding the loop and further testing. In some embodiments, once the test results and the calibrated expected results match, source 304 can be adjusted to provide another concentration of gas and the calibration process repeated. A more accurate calibration can be achieved by calibrating the response of sensor 102 over more than one concentration of gas provided by source 304.

In step 554, if the calibration sequence has completed, algorithm 540 proceeds to step 556 where timer 132 is started. In some cases, the calibration that results in the processing of sensor data from sensor 102 to an accurate result remains valid for a period of time. The time set in timer 132 in step 556 indicates when the results obtained will be again considered uncalibrate.

In some embodiments, calibration algorithm 540 can power down sensor 102 in step 558 when it is completed. In embodiments where algorithm 540 immediately exits to a measurement mode, algorithm 540 may leave sensor 102 powered. In step 560, the user is informed at user interface 126 that sensor 102 is calibrated and in step 562, algorithm 540 exits the calibration mode 406.

Once calibration is complete in mode 106 so that data read from sensor 102 can be used to accurately display a concentration of gas, then state function 400 proceeds to accurate measurement mode 408. In accurate measurement mode 408, mobile device 100 with sensor 102 can be used to measure and display measured gas concentrations. However, in some embodiments after a period of time, calibration will be lost. Consequently, after a period of time has elapsed, state function 400 will transition back to relative measurement mode 402. Again, during relative measurement mode 402 mobile device 100 and sensor 102 can provide relative measurements of gas concentration.

Figure 5D:
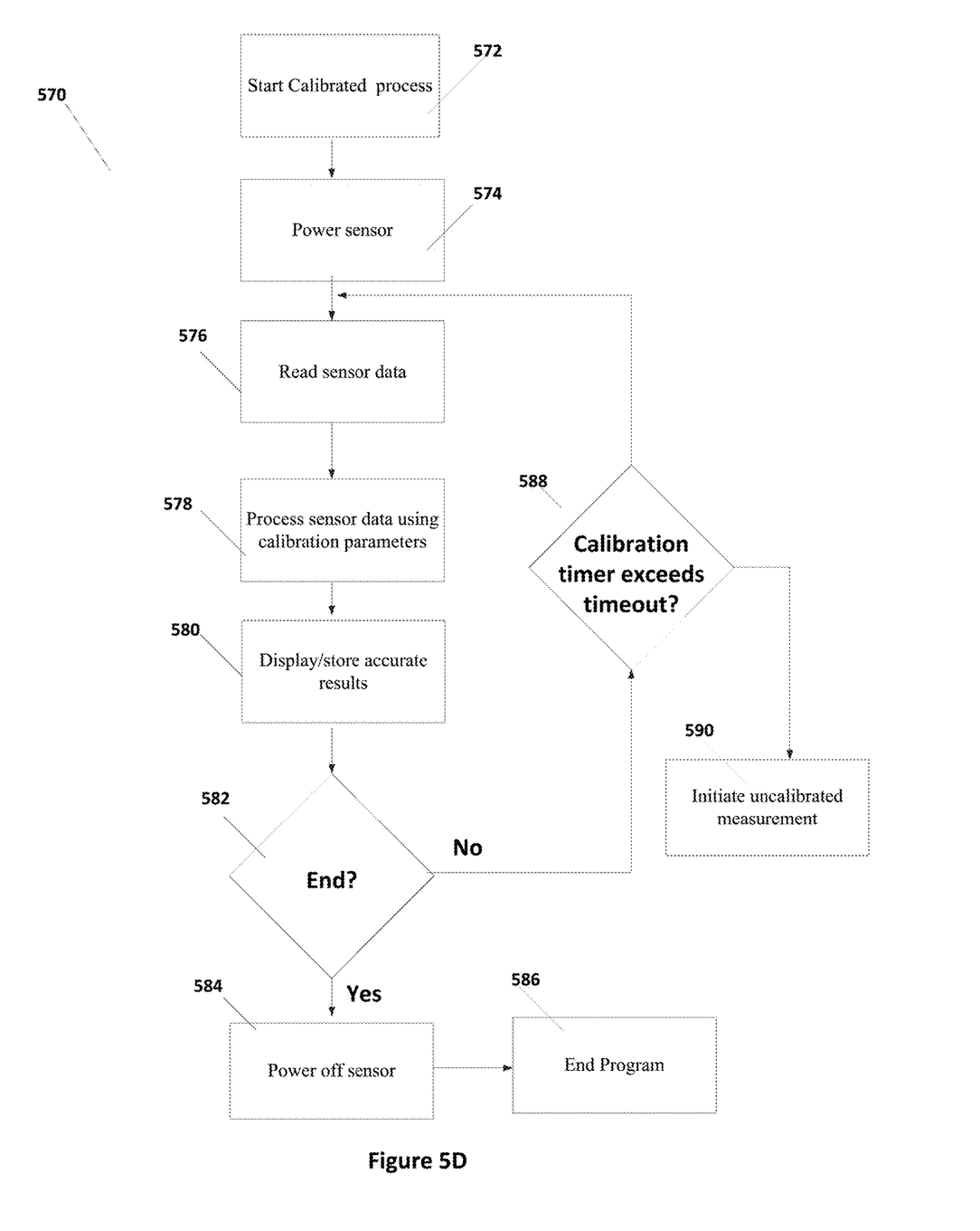

FIG. 5D illustrates an example algorithm 570 that is executed in accurate measurement mode 408. Step 572 is started after completion of algorithm 540 as illustrated in FIG. 5C and after instructions from a user at user interface 126 to begin measuring gas concentrations. In step 574, sensor 102 is powered. In step 576, sensor data is read from sensor 102. In step 578, the sensor data is processed according to the calibrated parameters. In step 580, the accurate gas concentration measurements are displayed at user interface 126. In some embodiments, the accurate gas concentration measurements are also stored in memory 122.

In step 582, algorithm 570 determines whether a user, through user interface 126, has stopped measurement. If yes, then algorithm 570 proceeds to step 584, where the power to sensor 102 is shut down, and then to step 586 where algorithm 570 is stopped. If, in step 582, measurement had not ended, then algorithm proceeds to step 588. In step 588, algorithm 570 checks timer 132. If the timer 132 has not exceeded the time limit, then algorithm 570 returns to step 576. If the time limit has been exceeded, then algorithm 570 proceeds to step 590. In step 590, algorithm 570 indicates to the user that measurement is no longer calibrated and algorithm 570 initiates algorithm 502 as illustrated in FIG. 5A.

The above detailed description is provided to illustrate specific embodiments of the present invention and is not intended to be limiting. Numerous variations and modifications within the scope of the present invention are possible. The present invention is set forth in the following claims.

What is claimed is:

1. A mobile device with a gas monitor, comprising:
 a gas sensor that measures gas concentration in a volume of gas;
 a mobile device coupled to the gas sensor, the mobile device including a processing unit executing instructions to:
  receive a request from a user of the mobile device;
  if the request is for calibrated data and if a previous calibration has expired,
   acquire calibration data for the gas sensor with a calibration device that provides a known gas to the gas sensor, and
   set a timer that expires when the calibration data has expired;
  read concentration data of the volume of gas from the gas sensor;
  provide calibrated concentration data based on the concentration data from the gas sensor with the calibration data if the calibration has not expired; and
  provide relative concentration data based on the concentration data from the gas sensor if the calibration has expired.

2. The mobile device of claim 1, wherein the instructions to acquire calibration data includes instructions to
 initialize for calibration that includes instructions to a user to provide the calibration device to the gas sensor;
 read data from the gas sensor in the presence of the known gas with known concentration provided by the calibration device; and
 compile the calibration data based on the data from the gas sensor and the known gas; and
 provide instructions to the user to remove the calibration device when calibration data has been acquired.

3. The mobile device of claim 2, wherein the instructions to initialize for calibration includes instructions to
 provide instructions to a user to configure a chamber of the calibration device to enclose the sensor; and
 provide instructions to the user to apply the known gas from a known source to the chamber.

4. A method of operating a mobile gas sensor with a mobile device, the mobile gas sensor being a gas sensor incorporated with the mobile device, comprising:
 receiving a request from a user of the mobile device;
 if the request is for calibrated data and if a previous calibration has expired,
  acquiring calibration parameters for the gas sensor using a calibration device that provides a known gas to the gas sensor, and
  setting a time that expires when the calibration parameters have expired;
 reading concentration data from the gas sensor, the concentration data indicating a concentration of gas within a volume of gas to be measured;
 providing a calibrated indication of gas concentration based on the concentration data and calibration parameters while the calibration parameters have not expired; and
 providing a relative indication of gas concentration based on the data if the calibration parameters have expired.

5. The method of claim 4, wherein providing calibration parameters includes
 initializing for calibration of the mobile gas sensor by instructing a user to configure the calibration device to enclose the gas sensor and provide the known gas of a known concentration to the gas sensor with the calibration device;
 receiving data from the gas sensor of the mobile gas sensor in the presence of the known gas;
 providing the calibration parameters based on the data from the gas sensor;
 and
 instructing the user to remove the calibration device.

6. The method of claim 5, wherein calibrating the mobile gas sensor is initiated on startup of the mobile device or by the user.

7. A mobile device, comprising:
 a processor;
 a memory coupled to the processor, the memory storing instructions executable by the processor and data;
 a user interface coupled to the processor;
 an interface configured to interface with a gas sensor, the interface further coupled to the processor,
 wherein the processor executes a gas monitoring algorithm under direction of a user through the user interface, the gas monitoring algorithm including
 a relative measurement mode, wherein in the relative measurement mode the processor executes instructions to measure a volume of gas and provide a relative indication of gas concentration to the user;
 a calibration initialization mode, wherein the calibration initialization mode is entered from the relative measurement mode when the user requests calibrated concentration data from the gas sensor, and wherein the processor executes instructions to direct the user to prepare for calibration by providing a calibration device with a known gas to the gas sensor;

a calibration mode, the calibration mode is entered from the calibration initialization mode, and wherein the processor executes instructions to acquire calibration data for the gas sensor with the calibration device that provides the known gas to the gas sensor and to set a timer that expires when the calibration data acquired has expired, and an accurate measurement mode, wherein in the accurate measurement mode the processor executes instructions to measure a volume of gas a provide a calibrated indication of gas concentration to the user.

8. The mobile device of claim 7, wherein the relative measurement mode is entered on receipt of a measurement request from the user interface or is transitioned to from the accurate measurement mode when calibration parameters obtained in the calibration mode have expired.

9. The mobile device of claim 8, wherein in the relative measurement mode the processor executes instructions to power the gas sensor;

read sensor data from the gas sensor;

determine that calibration parameters determined in the calibration mode have expired;

if the calibration parameters have expired, then process the sensor data to provide non-calibrated concentration results; and display the concentration results.

10. The mobile device of claim 7, wherein the calibration mode is entered from the initialization mode when confirmation of a calibration setup that includes configuring the calibration device to provide the known gas concentration to the gas sensor is received through the user interface.

11. The mobile device of claim 10, wherein the accurate measurement mode is entered from the calibration mode after calibration has been reached.

12. The mobile device of claim 11, wherein in accurate measurement mode, the processor executes instructions to power the gas sensor;

read sensor data from the gas sensor;

determine calibration parameters have not expired;

process the sensor data using calibrated parameters to obtain calibrated gas concentration data; and display the the calibrated indication of gas concentration data to the user.

13. The mobile device of claim 10, wherein in calibration mode the processor executes instructions to power the gas sensor;

read sensor data from the gas sensor, wherein the gas sensor has been configured to receive gas from a known source from the calibration device;

compare with expected results from the known source; and adjust calibration parameters to provide calibration during the accurate measurement mode.

14. The mobile device of claim 7, wherein in the initialization mode the processor executes instructions to instruct a user through the user interface to configure the calibration device with a chamber that encloses the gas sensor and to provide gas from a known source to the chamber; and receive from the user interface a confirmation that the chamber and known source are applied.

15. A method of operating a mobile device coupled to a gas sensor, comprising:

operating in a relative measurement mode when a calibration is not achieved or has expired, wherein in the relative measurement mode the method includes reading concentration data indicating a concentration of gas within a volume of gas to be measured and displaying a relative indication of gas concentration to a user on a user interface;

transitioning to a calibration initialization mode from the relative measurement mode when instructions are received from a user through the user interface, wherein during the calibration initialization mode a calibration setup where the user is instructed to provide a calibration device configured to provide a known gas to the gas sensor;

transitioning to a calibration mode from the calibration initialization mode when confirmation of the calibration setup is received through the user interface, wherein in the calibration mode the method includes acquiring calibration parameters using the known gas from the calibration device and setting a time that expires when the calibration parameters have expired;

transition to an accurate measurement mode from the calibration mode when the calibration parameters have been acquired; and transitioning to the relative measurement mode from the accurate measurement mode when the calibration parameters have expired.

\* \* \* \* \*